United States Patent
Niesen (10) Patent No.: US 11,980,603 B2
(45) Date of Patent: May 14, 2024

(54) METHOD OF TREATING EXPRESSIVE LANGUAGE DEFICIT IN AUTISTIC HUMANS

(71) Applicant: Charles E. Niesen, Pasadena, CA (US)

(72) Inventor: Charles E. Niesen, Pasadena, CA (US)

(73) Assignee: AMS Therapeutics, LLC, Pasadena, CA (US)

( * ) Notice: Subject to any disclaimer, the term of this patent is extended or adjusted under 35 U.S.C. 154(b) by 0 days.

(21) Appl. No.: 17/838,192

(22) Filed: Jun. 11, 2022

(65) Prior Publication Data

US 2023/0398094 A1    Dec. 14, 2023

(51) Int. Cl.
   *A61K 31/4015*    (2006.01)
   *A61P 25/00*    (2006.01)

(52) U.S. Cl.
   CPC .......... *A61K 31/4015* (2013.01); *A61P 25/00* (2018.01)

(58) Field of Classification Search
   CPC .......................... A61K 31/4015; A61P 25/08
   See application file for complete search history.

(56) References Cited

U.S. PATENT DOCUMENTS

| | | |
|---|---|---|
| 2004/0058997 A1 | 3/2004 | Daniel |
| 2006/0052428 A1 | 3/2006 | Chez |
| 2014/0142140 A1* | 5/2014 | Bird .................. A61K 31/4166 548/321.1 |
| 2019/0194287 A1 | 6/2019 | Bowrey et al. |
| 2021/0393636 A1 | 12/2021 | Sullivan |

FOREIGN PATENT DOCUMENTS

| | | |
|---|---|---|
| KR | 20140135676 A | 11/2014 |
| WO | 2020208564 A1 | 10/2020 |

OTHER PUBLICATIONS

Frye et al. "Traditional and non-traditional treatments for autism spectrum disorder with seizures: an on-line urvey", BMC Pediatrics (2011), 11:37 (http:/Awww.biomedcentral.com/147 1-243 1/11/37) (Year: 2011).*
Abou-Khalil, Continuum (Minneap Minn) 2016;22(1):132-156 (Year: 2016).*
Benitez-Burraco et al., Hypothesis and Theory (Aug. 2016), vol. 10, Article 373, pp. 1-23 (Year: 2016).*
Benitez-Burraco, Hypothesis & Theory 2016, vol. 10, (Year: 2016).*
Siniscalchi et al., Neurology & Neurotherapy Open Access Journal, 2016, vol. 1, Issue 1, pp. 1-7. (Year: 2016).*
Abou-Khalil, Continuum 2016, vol. 22(1), pp. 132-156. (Year: 2016).*

(Continued)

*Primary Examiner* — Craig D Ricci
*Assistant Examiner* — Janet L Coppins
(74) *Attorney, Agent, or Firm* — John D. Carpenter (57) ABSTRACT

A pharmacological method for treating the expressive language deficit in an autistic human child or adult is provided. A therapeutically effective dose of a succinimide anticonvulsant, e.g., ethosuximide, methsuximide, phensuximide, or a pharmaceutically acceptable salt thereof, is administered to a patient suffering from expressive language deficit, preferably over an extended period, e.g., six months or longer. Language gains are retained even after treatment is discontinued.

13 Claims, 3 Drawing Sheets

Expressive language changes after 6 months of ETS treatment (56) References Cited

OTHER PUBLICATIONS

Glauser et al., Epilepsia 2013, vol. 54 (1), pp. 141-155. (Year: 2013).*
Frye, R.E., et al., "Traditional and non-traditional treatments for autism spectrum disorder with seizures: an on-line survey", BMC Pediatrics (2011), 11:37 (http://www.biomedcentral.com/1471-2431/11/37).
Kaufman, K.R., "Antiepileptic Drugs in the treatment of psychiatric disorders", Epilepsy & Behavior 21 (2011), 1-11.
Landmark, C.J., "Antiepileptic Drugs in Non-Epilepsy Disorders", CNS Drugs 2008: 22(1):27-47.
Moon, K.T., "What is the Best Treatment for Childhood Absence Epilepsy?", American Family Physician Jan. 1, 2011; 83(1), 81-82 (https://www.aafp.org/pubs/afp/issues/2011/0101/p81a.html).
Parnas, J., et al., "Psychotropic effect of antiepileptic drugs", Acte Neurol. Scandinav. (1971) vol. 60, 329-343.
Smith, W.L., et al., "Psychometric Study of Children with Learning Problems and 14-6 Positive Spike EEG Patterns, Treated with Ethosuximide (Zarontin) and Placebo*'", Archives of Disease in Childhood, 1968, vol. 43, 616-619.
Prior Use of Ethosuximide Before Filing Date—see Letter Accompanying Information Disclosure Statement, submitted herewith.

Sikich, L., et al., "Intranasal Oxytocin in Children and Adolescents with Autism Spectrum Disorder," The New England Journal of Medicine, 385; 16, Oct. 14, 2021, pp. 1462-1473.
Jacob, S., et al. "Large multicenter randomized trials in autism: key insights gained from the balovaptan clinical development program," Molecular Autism (2022) 13:25 https://doi.org/10.1186/s13229-022-00505-6 (11 pages).
Zimmerman, A., et al., "Randomized controlled trial of sulforaphane and metabolite discovery in children with Autism Spectrum Disorder," Molecular Autism (2021) 12:38 https://doi.org/10.1186/s13229-021-00447-5 (22 pages).
Canitano, R., et al., Autism with Epilepsy: A Neuropsychopharmacology Update, Genes 2022, 13, 1821. https://doi.org/10.3380/genes13101621 (10 pages).
Gilberg, C., "The Treatment of Autism," Journal of Autism and Developmental Disorders, vol. 21, No. 1, 1991, pp. 61-77.
Shinar, R., et al., "Pretreatment behavior and subsequent medication effects in childhood absence epilepsy," Neurology 89 Oct. 17, 2017, pp. 1698-1706.
ISA/US—International Search Report and Written Opinion (ISR/WO) from Applicant's counterpart international application, No. PCT/US 23/25059 (filed Jun. 12, 2023), dated Sep. 28, 2023.
Castillo et al., Speech-Stimulating Substances in Autism Spectrum Disorders, Behav. Sci. 2019, 9, 60.

* cited by examiner

METHOD OF TREATING EXPRESSIVE LANGUAGE DEFICIT IN AUTISTIC HUMANS

BACKGROUND OF THE INVENTION

The invention relates to pharmacological methods for treating the expressive language deficit exhibited by children and adults who suffer from autism.

The term "autism spectrum disorder" (ASD) is used by neurologists to describe a range of conditions whose main feature is poorly developed/limited social interaction. Conditions typically present by age 2 and are reported to affect 1 out of 44 children in the United States, and as many as 75 million children worldwide. Patients suffering from ASD may exhibit social awkwardness or even ignore and refuse to interact with others. Autism lies at one end of the spectrum and is characterized by the patient being uninterested in interacting with other people. They ignore their parents as well as their peers. Also distinct in this group is their expressive language/communication deficit. Most autistic patients develop little to no expressive language, remaining mute, poorly communicative, and isolated their whole lives. Their language is rarely spontaneous. The urge to communicate is missing. They may develop 2-3 word phrases, but these phrases are said only in response to questions and not out of a want or desire to talk.

For example, an autistic person may be able to answer the question "What did you do this weekend?" but then lack the ability to add to or carry on a conversation. They may answer, "Saw movie," but will not pursue the conversation with "And what did you do?" or "I saw a good movie. Have you seen this movie?" Thus, the central language/communication disorder in autism is characterized by not only 1) paucity of expressive language, but 2) inability to converse, to have a mutual and reciprocal exchange of words. The term "autism" was coined by Dr. Kanner in 1945 to describe this unique set of language and behavior problems he encountered in his young patients. These children did not want to communicate. They preferred to be alone, away from others, autonomous, hence autism.

This language deficit in autism stands in contrast to the communication problems in other ASD patients, specifically Asperger syndrome and pervasive developmental disorder (PDD). Patients with Asperger syndrome do not have a language/communication disorder. They speak in full sentences which are easily understood. They can carry on a conversation. Their deficit is a social one. They prefer limited social interaction and are awkward and unfamiliar with simple social discourse. They tend to be smart, often with better skills and more interest in the hard sciences, such as engineering or computer science. Patients with PDD, on the other hand, tend to have attention and learning problems and are often several grade levels below their peers. As such, they do not know how to have a conversation, even though they may want to and can talk in full sentences. They are socially awkward. In conversation, they talk mainly about their own interests, in great detail, without engaging or showing interest in the other person's feelings or activities. For example, they will talk about their interest in dinosaurs or a computer game to the exclusion of what the other person wants to say.

Patients with mental retardation are not considered part of the ASD group. They may have simple or limited expressive language, but they are interactive and interested in being with other people. They will engage, gesture, hug, and try to communicate with others, unlike autistic patients who ignore others, often refusing to acknowledge even their presence.

There is currently no FDA-approved treatment for childhood autism. Few if any pharmacological interventions specifically target expressive language.

Individuals with ASD are generally at higher risk of developing epilepsy, but the relationship between ASD and epilepsy is complex. Although antiepileptic drugs (AEDs) such as valproate, lamotrigine, levetiracetam, and others have been used extensively to treat other disorders, both in neurology and psychiatry, the medical community has not recognized that AEDs could have a role to play in treating expressive language deficit in autistic patients. For example, a 2008 review article (Landmark, C. J., *Antiepileptic Drugs in Non-Epilepsy Disorders*, CNS Drug Review, 2008: 22(1): 27-47) lists several first and second-generation AEDs and their use in the treatment of many disorders, but does not mention autism, ASD, or expressive language deficit. The antiepileptic drug ethosuximide is not listed or discussed in the article.

Kaufman, K. R., *Antiepileptic Drugs in the treatment of psychiatric disorders*, Epilepsy & Behavior 21 (2011), 1-11, provides an overview of 21 AEDs "in which negative psychotropic properties, approved indications in psychiatry, off-label studies used in psychiatry, and principal uses in psychiatry are presented with literature review." Ethosuximide is discussed on page 2, where the author notes that there are no approved indications or principal uses for ethosuximide in psychiatry, though there have been off-label uses for treatment of bipolar disorder. In Table 2, Kaufman indicates that ethosuximide has been studied as a possible treatment for affective disorders.

A 2011 BioMed Central research article, Frye, R. E., et al., *Traditional and non-traditional treatments for autism spectrum disorder with seizures: an on-line survey*, BMC Pediatrics (2011), 11:37 (http://www.biomedcentral.com/1471-2431/11/37), describes the results of an online survey completed by parents of children with ASD and epilepsy. This study evaluated the effects of several AEDs (valproic acid, lamotrigine, levetiracetam, ethosuximide, and others) and non-AED treatments on seizure control and other facets of the patients' lives. As compared to non-AED treatments, AEDs were perceived as improving seizures but worsening other clinical factors, i.e., sleep, communication, behavior, attention, and mood.

KR20140135676 (Soo et al.)—English language abstract—discloses compositions for preventing and treating "concentration disorder" diseases—attention deficit hyperactivity disorder, schizophrenia, frontal lobe epilepsy, and autism. Several nonspecific T-type calcium channel inhibitors are listed, including mibefradil, tetramethrin, ethosuximide, SUN-N8075, and others.

US2004/0058997 (Daniel et al.) discloses a method for treating "disorders of personal attachment and deficient social interaction" in which an anticonvulsant medication (e.g., valproic acid, valproate, or its enteric coated derivatives, carbamazepine, oxcarbazepine, zonisamide, lamotrigine, ethosuximide, felbamate, levetiracetam, methsuximide, phenytoin, primidone, tigabine, topiramate) is administered to the patient. Autism is not mentioned, and no efficacy data is provided. Disorders that might benefit from the treatment process are listed, including "schizoid personality disorder, schizotypal personality disorder, avoidant personality disorder, paranoid personality disorder, Asperger's syndrome, pervasive developmental disorder, and clinically significant social introversion that does not meet the threshold for a formal psychiatric disorder by current diagnostic standards such as DSM-IV."

WO2020/208564 (Roman et al.) discloses carbamoyl cyclohexane derivatives for treating ASD, attention deficit hyperactivity disorder (ADHD), and other conditions. The derivatives are to be used alone or in combination with one or more adjunctive therapeutic agents selected from a broad set of pharmaceuticals: psychostimulants/nootropics, antipsychotics, antidepressants, anxiolytics, antihypertensives, antiepileptics, narcotics, and spasmolytics.

Efficacy data was generated using a rodent model of ASD based on prenatal exposure to valproate (valproic acid, VPA), and the effect of the derivatives on socio-communicational function in ASD-phenotype rat pups was evaluated by monitoring maternal deprivation-induced ultrasonic vocalization. Efficacy data from humans are not disclosed.

US2019/0194287 (Bowrey et al.) discloses a treatment for various neuropsychiatric disorders, neurodegenerative diseases, and cerebrovascular accidents, wherein a viral vector containing a Designer Receptor Exclusively Activated by Designer Drug (DREADD) is administered to a patient's eye. After the DREADD is expressed, an agonist is administered to the expressed DREADD. In one embodiment, one or more additional therapeutic agents—selected from a group of more than 200 listed compounds—is also administered to the patient. Autism is identified as one of 13 neuropsychiatric disorders, but no data specific to autism—let alone expressive language deficit—is disclosed.

SUMMARY OF THE INVENTION

The present invention provides a pharmacological method of treating the expressive language deficit in an autistic human. A therapeutically effective amount of a succinimide anticonvulsant—e.g., ethosuximide, methsuximide, phensuximide, or a pharmaceutically acceptable salt thereof—is administered to the autistic human, preferably for an extended period of time. In one embodiment, the drug is administered daily, or twice daily, for at least one month, more preferably at least three months, more preferably at least six months, thereby improving the person's expressiveness and ability to converse with others.

BRIEF DESCRIPTION OF THE DRAWINGS

The invention is better understood when considered with the appended drawings, which are graphs illustrating the effect of administering ethosuximide ("ETS") to autistic patients, over time, in accordance with one aspect of the invention.

DETAILED DESCRIPTION

In a first aspect of the invention, a pharmacological method is provided for treating the expressive language deficit in an autistic human child or adult. A therapeutically effective dose of a succinimide anticonvulsant is administered to a patient suffering from expressive language deficit, preferably over an extended period of time, e.g., one month, two months, three months, six months, or longer. Nonlimiting examples of succinimide anticonvulsants include ethosuximide, methsuximide (also known as mesuximide), and phensuximide, whose structural formulas (I-III) are shown below:

Ethosuximide (2-ethyl-2-methylsuccinimide):

I

Methsuximide (N,2-dimethyl-2-phenylsuccinimide):

II

Phensuximide (N-methyl-2-phenylsuccinimide):

III

The use of ethosuximide, methsuximide, and phensuximide as anti-epileptic drugs is well established. Ethosuximide is the drug of choice for treating childhood absence seizures. It is known to block T-type calcium channels and is not known to affect mood or behavior.

Ethosuximide is sold by Pfizer Inc. (NY, NY) under the brand name Zarontin®. It is available in capsule and syrup forms. Methsuximide is also sold by Pfizer, under the brand name Celontin®. Phensuximide is sold under the trademark Milontin®.

As an alternative to using any of the anticonvulsant compounds of formulas I-III, a pharmaceutically acceptable salt thereof is administered to the autistic patient, preferably over an extended period, e.g., 1-6 months or longer. A nonlimiting example is ethosuximide hydrochloride, prepared by treating ethosuximide with hydrochloric acid. More generally, any pharmaceutically acceptable salt of ethosuximide, methsuximide, or phensuximide can be utilized. Synthetic methods for preparing pharmaceutical salts are found in standard texts, such as the Handbook of Pharmaceutical Salts (P. Heinrich Stahl and Camille G.

Wermuth, eds.), published jointly by Verlag Helvetica Chimica Acta (Zurich, Switzerland) and Wiley-VCH (Weinheim, Germany), 2008, chapter 11, pp. 249 et seq., incorporated by reference herein.

An autistic patient who exhibits expressive language deficit symptoms should be evaluated by a child neurologist before treatment begins, with particular attention given to the patient's language abilities and limitations. In one embodiment of the invention, ethosuximide, methsuximide, or phensuximide, or a pharmaceutically acceptable salt of ethosuximide, methsuximide, or phensuximide, is administered to the patient. The patient's language skills should be evaluated before treatment commences, and periodically during the course of treatment. It is preferred to administer the drug at least daily for at least one month, more preferably at least two months, more preferably at least three months, and even more preferably for six months or longer. Although the drug can be administered once a day, good results are seen with twice per day (b.i.d.) administration.

Drug dosage depends on the age and weight of the patient, with younger, lighter patients typically receiving a smaller dose than older children, teenagers, and adults. Dosage can be expressed as milligrams of drug per kilograms of body weight per day (mg/kg/day), or on an absolute basis (e.g., 1000 mg/day), a twice per day (b.i.d.) basis (e.g., 500 mg b.i.d.), etc. In one embodiment, the drug is administered at a dosage of 10-60 mg/kg/day. For younger, smaller children, a suitable dosage range is 20-40 mg/kg/day, 20-30 mg/kg/day, or 20-22 mg/kg/day. Positive effects are even seen at dosages as low as 10 or 11 mg/kg/day. For teenagers and adults, a suitable dosage is 150-1000 mg b.i.d., more preferably 500-1000 mg b.i.d.

Two nonlimiting illustrations may be helpful: (1) 5-year-old patient weighing 44 lb (20 kg); dosage: (22 mg/kg/day)×20 kg=440 mg/day or 220 mg b.i.d. (2) 15-year-old patient weighing 110lb (50 kg); dosage: (40 mg/kg/day)×50 kg=2000 mg/day, or 1000 mg b.i.d.

Experimental Methods, Examples, and Results

To assess the effectiveness of ethosuximide as a pharmacological treatment for expressive language deficit, 24 human patients were treated with ethosuximide (ETS) for at least one month, more preferably six months or longer, and their language, social, and behavioral skills were monitored throughout the course of treatment, typically every 1-3 months. Study participants (subjects) were divided into four treatment groups based on neurodevelopmental level (mental status): normal IQ (NIQ), borderline IQ (BIQ), mild mental retardation (mMR), and moderate mental retardation (moMR). Language skills (expressiveness, receptivity), social behavior (social interaction, eye contact, participation), and mood (affect, irritability, agitation) were evaluated at various points in time. Verbal output was graded using a 7-point scale (0-6), where 0=nonverbal, 1=echolalic (the patient can respond by echoing the speaker), 2=single words (the patient can respond in single words), 3=phrases (the patient can respond in a simple phrase), 4=sentences (the patient can respond in a full sentence), 5=spontaneous speech (the patient can speak spontaneously), and 6=mutual speech (the patient can have a true conversation with another person). The 7-point scale for evaluating expressive language is summarized in Table 1.

TABLE 1

Expressive Language Scale

| Ability | Abbreviation | Numeric Rating |
|---|---|---|
| Mutual speech | MU | 6 |
| Spontaneous speech | SP | 5 |
| Sentences | SN | 4 |
| Phrases | PH | 3 |
| Single Words | SW | 2 |
| Echolalic | EC | 1 |
| Non-verbal | NV | 0 |

Social behavior and mood symptoms, based on those described in the Aberrant Behavior Checklist, an established behavioral rating system used in evaluating patients with intellectual disabilities (see Aman, M. G., et al., "*The Aberrant Behavior Checklist: A behavior rating scale for the assessment of treatment effects,*" American Journal of Mental Deficiency, 89(5):485-491 (1985), incorporated by reference herein), were also graded on a 7-point scale (0±3). Patients had a zero value at baseline (score before treatment) and were given a positive score (+1 to +3) or negative score (−1 to −3) if their symptoms improved or worsened to a mild, moderate, or significant degree, respectively. Social behavior and mood data are presented below in Table 8.

Patient demographics (number, gender, age, mental status, prescription dosage, and length of treatment (Rx) are summarized in Table 2.

TABLE 2

Patient Demographics

| Total number of patients (N): | 24 |
|---|---|
| Gender: | 23 male, 1 female |
| Age (years): | 3-24 (av. 13.1 yrs.) |
| Number of patients (N) by age group: | |
| 3-9 years: | 9 |
| 10-14 years: | 5 |
| 15-25 years: | 10 |
| Number of patients (N) by mental status: | |
| normal IQ | 9 |
| borderline IQ | 5 |
| mild mental retardation | 7 |
| moderate mental retardation | 3 |
| Dosage Range: | 150-1000 mg b.i.d. |
| Rx Duration: | 1 mo. or more (av. 11.2 mos.) |

Tables 3 and 4 provide additional details of patient demographics, based on mental status and duration of treatment.

TABLE 3

Patient Age, Grouped by Patient Mental Status

| Patient Mental Status | N | Av. Age (yrs.) | Range (yrs.) | <10 yrs. old |
|---|---|---|---|---|
| NIQ | 9 | 9.5 | 3-19 | 5/9 |
| BIQ | 5 | 14.0 | 4-19 | 1/5 |
| mMR | 7 | 13.2 | 8-18 | 3/7 |
| moMR | 3 | 21.0 | 18-24 | 0/3 |

MS = mental status;
N = number of patients;
NIQ = normal IQ;
BIQ = IQ borderline between normal and mild mental retardation;
mMR = mild mental retardation;
moMR = moderate mental retardation

TABLE 4

Length of ETS Treatment, Grouped by Patient Mental Status

| Patient Mental Status | Duration of Treatment | | |
|---|---|---|---|
| | <6 mos. | 6-12 mos. | >12 mos. |
| NIQ | 2 | 7 | — |
| BIQ | 3 | — | 2 |
| mMR | 5 | — | 2 |
| moMR | — | — | 3 |

Entries refer to the number of patients per group and the length of treatment with ETS.
MS = mental status;
N = number of patients;
NIQ = normal IQ;
BIQ = IQ borderline between normal and mild mental retardation;
mMR = mild mental retardation;
moMR = moderate mental retardation It is common for autistic patients to receive one or more medications as treatment for a variety of conditions and symptoms, including attention deficit/hyperactivity disorder, irritability, mood swings, anxiety, seizures, etc. Many of the subjects receiving ETS treatment as described herein were concomitantly taking other medications, either intermittently or throughout the course of the ETS trial. These are summarized in Table 5.

TABLE 5

Number and Type of Concomitant Medications

| Patient Mental Status | | Concomitant Medications | | |
|---|---|---|---|---|
| MS | N | Range | Average | Most common |
| NIQ | 9 | 0-3 | 1.1 | Lisdexamfetamine, clonidine |
| BIQ | 5 | 1-2 | 1.6 | Aripiprazole, clonidine |
| mMR | 7 | 0-5 | 2 | Valproate, risperidone, alprazolam |
| moMR | 3 | 2-4 | 3 | Aripiprazole, lacosamide, oxcarbazepine, gabapentin |

MS = patient mental status;
N = number of patients;
Range = number of medications taken in addition to ethosuximide;
Average = average number of additional medications taken;
NIQ = normal IQ;
BIQ = IQ borderline between normal and mild mental retardation;
mMR = mild mental retardation;
moMR = moderate mental retardation;
Range = overall number of additional drugs taken per patient;
Average = average number of additional drugs taken per patient As can be seen from Table 5, subjects in the NIQ and BIQ groups typically were taking fewer concomitant medications than subjects in the mMR and moMR groups.

To evaluate drug efficacy and onset of action, each patient was monitored for changes in language, social behavior, and mood at various times after commencement of ETS therapy. Performance characteristics observed for each function (expressive language, mood, behavior) are summarized in Table 6, at t=1 month after commencement of treatment and t=3 months after commencement of treatment.

TABLE 6

ETS Treatment - Observations of Onset of Action

| | Observed performance after commencement of treatment | |
|---|---|---|
| Function | After 1 month | After 3 months |
| Expressive language | Increased word count (+1) (talking more) | 2-word phrases Listening better makes wants clearer |
| Social behavior | Increased eye contact (+1) More engaged | Sits in groups |
| Mood | Calmer (+1) More focused (+1) | Fewer tantrums |

Figure 1:
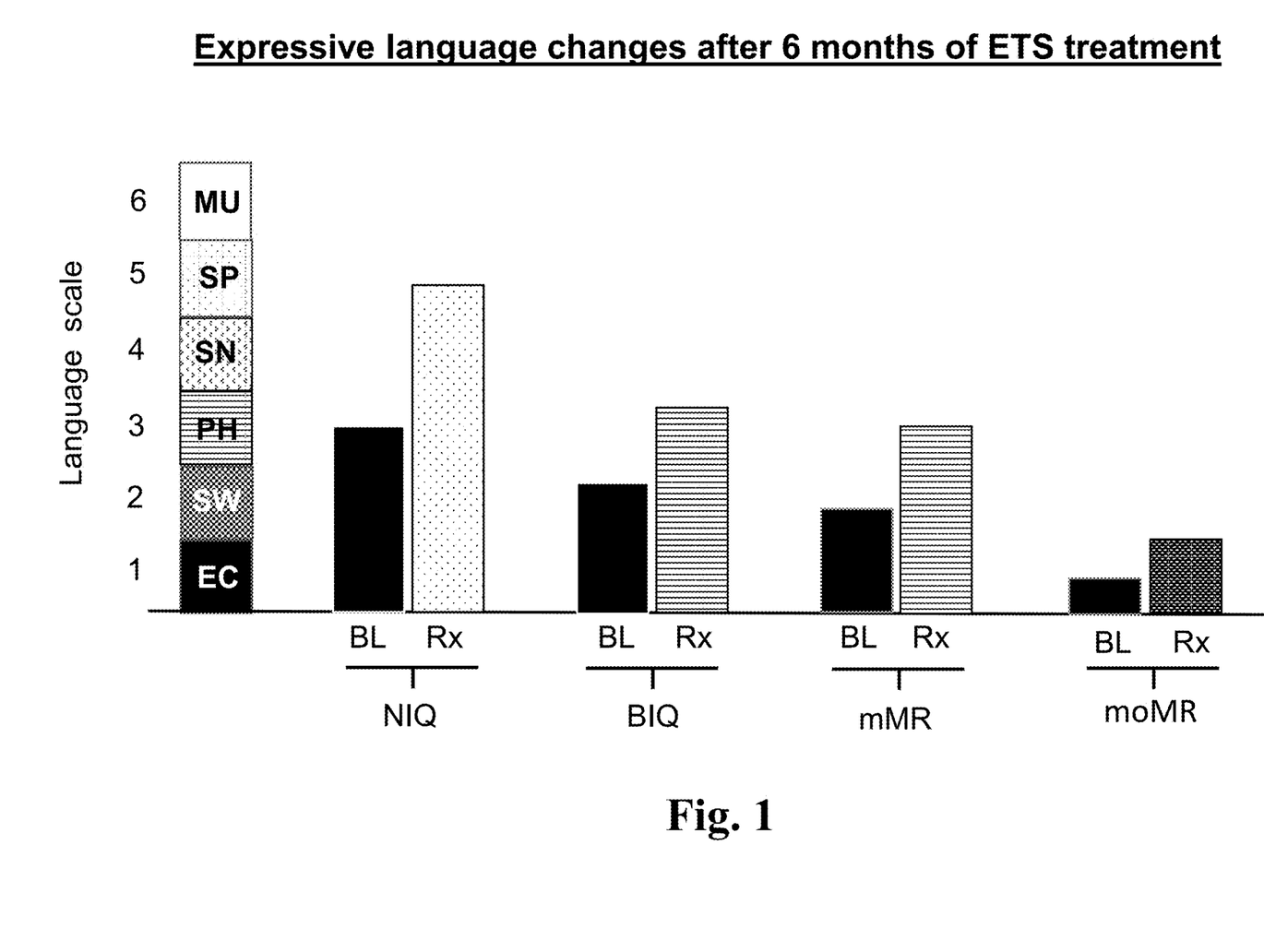
FIG. 1 is graph presenting changes in expressive language in patients treated with ethosuximide for at least six months, according to one embodiment of the invention.

The overall effectiveness of ethosuximide as a treatment for expressive language deficit is illustrated in FIG. 1, which presents expressive language scores as a set of histograms for the four mental status groups (NIQ, BIQ, mMR, and moMR). Subjects were scored prior to treatment (baseline, BL) and after six months (Rx). FIG. 1 presents data for patients who received ETS therapy for more than one month. The number of subjects in each group (N), and the mean expressive language scores at baseline (BL) and after six-months (Rx) can be summarized as follows: For subjects in the NIQ group (N=8), expressive language increased from 2.5 to 4.4. For the BIQ group (N=4), the mean score increased from 1.7 to 2.75. For the mMR group (N=6), the mean score increased from 1.3 to 2.5. For the moMR group (N=2), the mean score increased from 0.5 to 1.0. For each group, N reflects the number of patients who received ETS therapy for more than one month.

All four groups of patients improved after ETS treatment. The improvement in expressive language scores seen in the normal IQ group (N=8) are particularly impressive. The average (mean) score for these 8 patients increased to 4.4 by the end of the trial, an improvement of approximately 2 points (1.9). Remarkably, their language skills improved, on average, from the ability to use some words or speak in phrases to the ability to respond in full sentences or even speak spontaneously.

Figure 2:
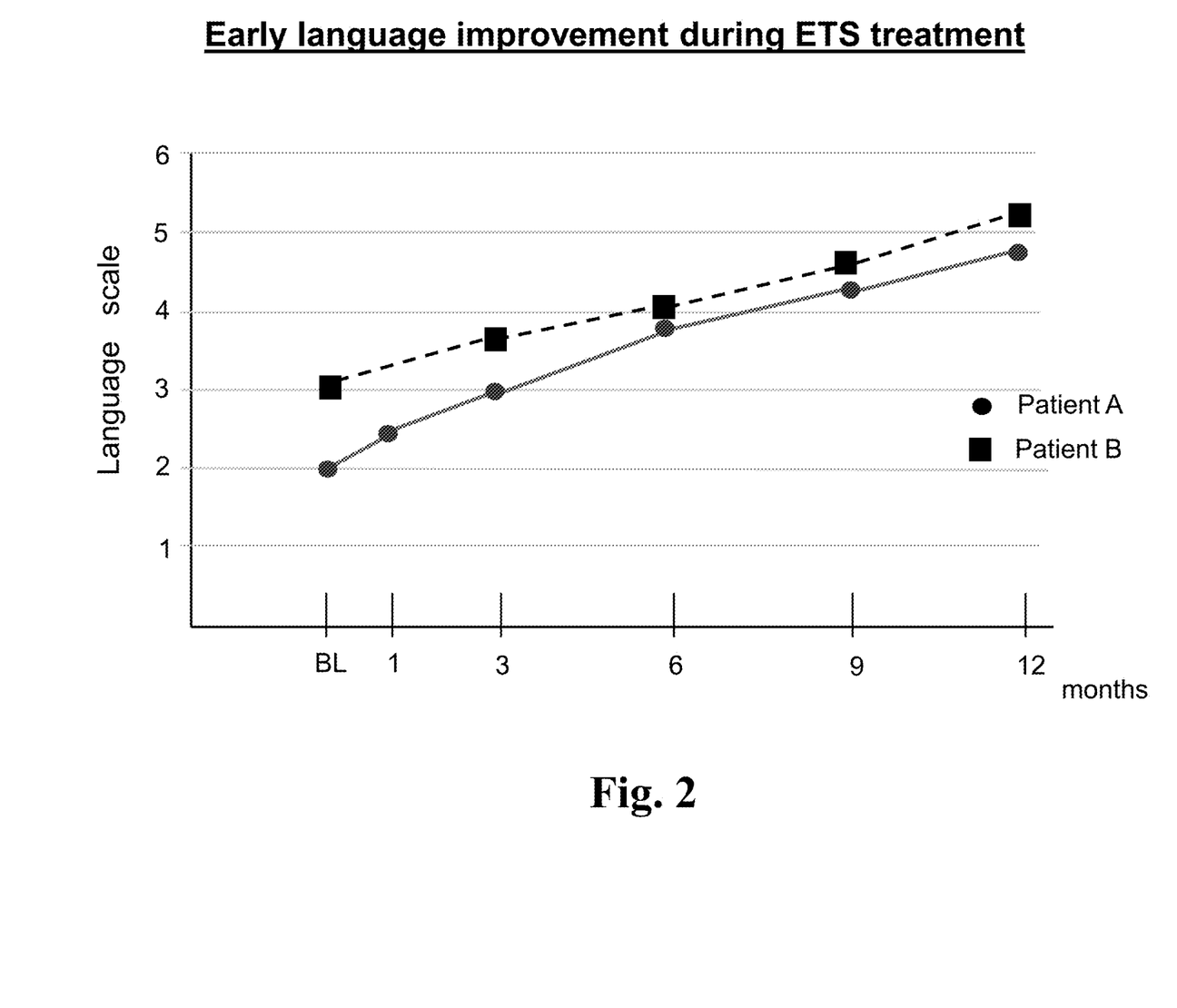
FIG. 2 is a graph presenting expressive language improvement in two autistic patients, ages 3.5 and 12 years old, who were treated with ethosuximide for one year according to one embodiment of the invention.

FIG. 2 presents expressive language data for two autistic subjects treated with ETS according to the invention: Patient A, a 3-and-a-half-year-old boy with absence epilepsy and normal IQ, and Patient B, a 12-year-old boy also with normal IQ. Both patients exhibited some spontaneous speech by 9 months from the commencement of treatment with ETS.

Patient A's expressive language improved slowly in the first three months of ETS treatment. When initially evaluated (Baseline, BL), he could say single words only (a score of 2). One month after the onset of ETS treatment, he was saying more words. He progressed from using single words to using phrases (a score of 3) after 3 months. At 6-9 months, he was responding in full sentences, and at 9-12 months he could speak spontaneously and even ask questions.

For Patient B, a similar improvement in speech was noted over 6-9 months. Before treatment, Patient B was echolalic and said some two-word phrases. Three months after onset of treatment with ETS, he seemed more focused and calmer. He said 3 and 4-word phrases. By month 6, Patient B could speak in sentences, and by month 9, he was able to converse spontaneously at times.

Table 7 provides specific examples of the improvement in expressive language exhibited by Patients A and B at various times during ETS treatment.

TABLE 7

ETS Effect on Language Development - Two Patients' Histories

| Patient | Age | Baseline | 1 mo. | 3 mo. | 6 mo. | 9 mo. | 12 mo. |
|---|---|---|---|---|---|---|---|
| A | 3.5 | SW | Increased words | PH "I want" "All done" | SN/SP "Thank you" Waves "hi" | SN/SP "Leave me alone" | SN/SP/MU Mom: "Wait a minute" Patient A: "OK, mom" |
| B | 12 | EC/ 2-word PH | — | 4-word PH focused calmer | SN "No, TV I want" | SN/SP "Cook me steak, Dad" | |

EC = echolalic;
SW = single words;
PH = phrases;
SN = sentences;
SP = spontaneous speech;
MU = mutual speech (true conversation with another person)

The effect of ethosuximide on language acquisition over time paralleled the time course of language development in normal (non-autistic) children. A non-autistic child, age 12-15 months, typically has a vocabulary of 4-6 words and can answer simple questions nonverbally. Spoken words may not always be clear. By age 18-23 months, vocabulary may increase to 50 words, and the child can use 2-word phrases and even combine words, such as "more milk." From age 2-3 years, the child can use 3-word sentences. The data in FIGS. 2 and 3 reveal a similar trend of progression for autistic children treated with ethosuximide over a period of six months or longer.

Patients younger than 12 years old who were taking ETS also received speech and ABA (Applied Behavioral Analysis) therapy. Speech therapy was often given twice a week for 30 minute sessions, while ABA therapy was given 5 days per week, 2-3 hours per day. ABA therapy is directed at training autistic patients to be more engaged in social settings and has less to do with spoken language. These two therapies were helpful because they provided patients an opportunity to practice language skills in a supportive environment to improve language and social skills. Their role cannot be underestimated, but it is not easily measured.

Ethosuximide was well tolerated in all ages evaluated. Common side effects reported in the literature for patients receiving ethosuximide treatment for childhood absence epilepsy include abdominal distress, diarrhea, weight loss, hyperactivity, lethargy, leukopenia, and depression. Very few of these symptoms were reported or observed in the patients participating in the study herein described. Eleven patients stopped ETS treatment after 6 months or less. Five of these patients dropped out for non-medical reasons.

Figure 3:
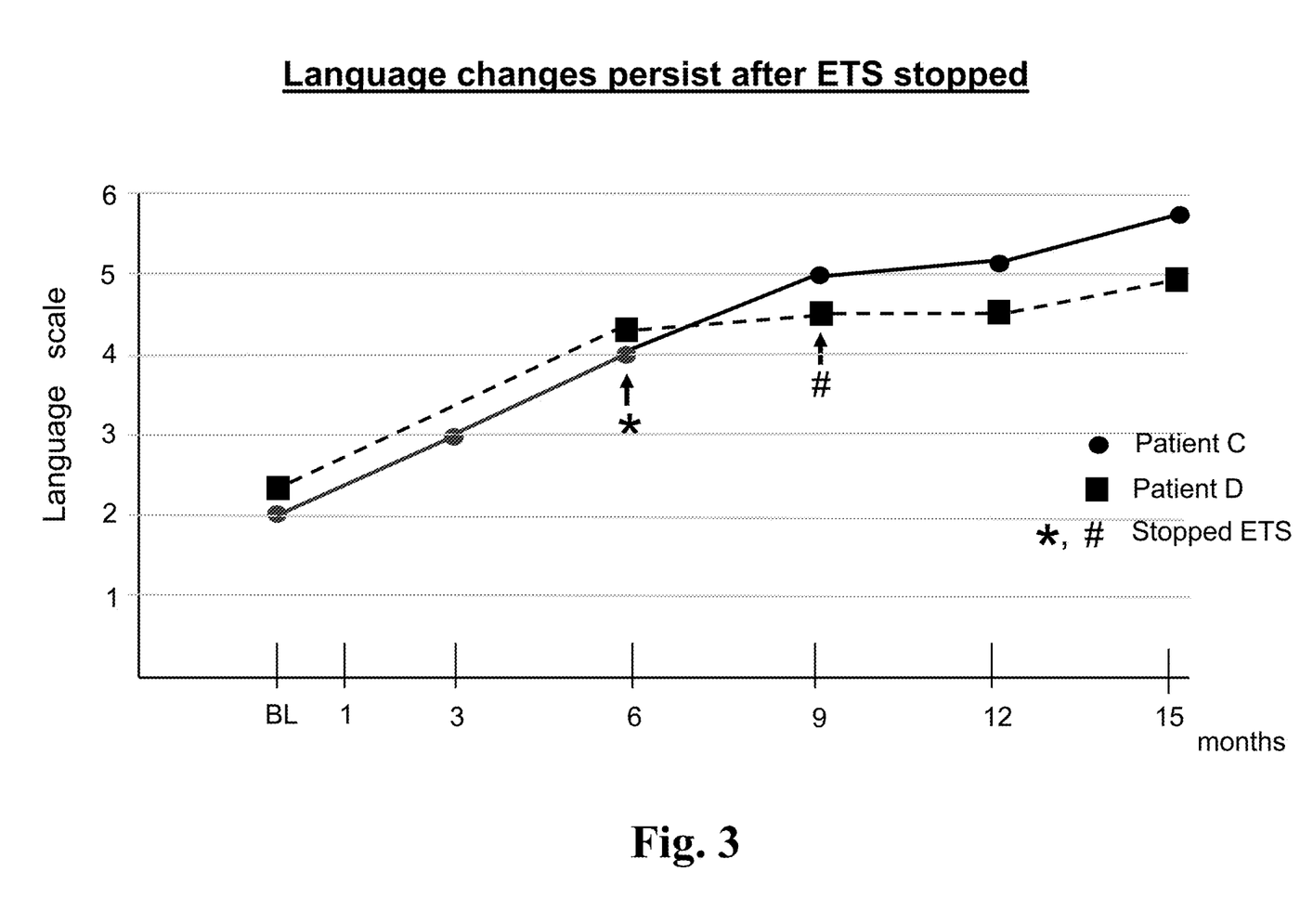
FIG. 3 is a graph presenting expressive language improvement in two autistic patients, ages 3 and 12 years old, who were treated with ethosuximide for six and nine months, respectively, according to one embodiment of the invention, and the retention of their improved language skills even after treatment was discontinued.

Patients who received ETS treatment for six months or longer exhibited the most improvements in expressive language skills. Notably, when treatment was discontinued after six months, patients did not lose their language gains. FIG. 3 graphs expressive language progression for two patients who stopped ETS treatment after six months. Patient C was a 3-year old autistic girl, and Patient D was a 12-year old autistic boy. The time when the two patients discontinued ETS treatment is denoted by * and #, respectively. Patient C received ETS treatment for 6 months and her expressive language skills steadily improved. She then discontinued treatment. Patient D discontinued treatment after 9 months. Notably, even after ETS treatment was stopped, the patients' language skills did not decline or stall. In fact, it continued to improve for both patients, as evaluated several months later. This suggests that ethosuximide may activate dormant language networks in the brain.

Advantageously, treatment with ethosuximide also yields improvements in other symptom domains, e.g., social behavior and mood, with the biggest gains seen in patients who exhibit the most expressive language skill improvement. Table 8 shows the improvement over baseline in expressive language, social behavior, and mood after six months of ETS therapy. Patients having normal IQ who were treated with ethosuximide for more than one month had a mean improvement in expressive language skills of about 2 points on the 7-point scale of Table 1. Equally impressive were the gains seen in social behavior and mood: +2 points and +1.2 points, respectively, using the Aberrant Behavior Checklist methodology described above. All groups improved in social behavior after six months of ETS therapy, especially the NIQ group. Most groups improved in mood, except the moMR group, which showed no change.

TABLE 8

ETS - Improvements in Expressive Language, Social Behavior, and Mood

| | Improvement Over Baseline | | |
|---|---|---|---|
| Mental Status (MS) | Expressive language | Social behavior | Mood |
| NIQ | +2.0 | +2.0 | +1.2 |
| BIQ | +1.0 | +1.5 | +1.4 |
| mMR | +1.2 | +1.0 | +1.0 |
| moMR | +0.5 | +1.0 | 0.0 |

MS = mental status;
N = number of patients;
NIQ = normal IQ;
BIQ = IQ borderline between normal and mild mental retardation;
mMR = mild mental retardation;
moMR = moderate mental retardation Although ethosuximide is typically prescribed to treat absence epilepsy, the beneficial effect of ETS treatment on expressive language provided by the invention is not due to ethosuximide's anti-epileptic effect. Of the 24 autistic patients discussed here, only seven had epilepsy. Three had childhood absence epilepsy and four had focal epilepsies. ETS treatment improved the expressive language skills of both epileptic and non-epileptic patients.

Ethosuximide is known to block T-type calcium channels, but its mechanism of action in reducing the expressive language deficit in autistic patients remains undetermined.

Without being bound by theory, it is possible to conjecture that ethosuximide acts on the brain's endocannabinoid system, or in novel networks that affect neurodevelopment.

Regardless of its mode of action, several things can be noted. Improvements in expressive language and social skills were evident in autistic patients even one month after commencing daily treatment with ethosuximide. These improvements progressed during treatment. The most gains occurred in patients who were treated for six months or longer. The best results were seen in younger patients and in patients with normal IQ, especially when ethosuximide treatment was coupled with language therapy, and/or applied behavioral analysis (ABA) therapy. (Older children in the study tended to have more behavioral problems and often were not receiving social therapy.) Ethosuximide also works in adults, especially if coupled with daily ABA therapy or similar therapy. Most notably, patients who discontinued treatment did not lose their language gains.

Ethosuximide drug therapy can be used to treat the expressive language deficit in autistic patients, including patients who are nonepileptic (not experiencing clinical seizures), patients who are epileptic (have experienced seizures), and patients who manifest epileptiform abnormalities on electroencephalograph (EEG) but have not experienced clinical seizures.

Upon reading this disclosure, it will be apparent to the skilled person that the invention can be characterized in another way, namely, the invention comprises ethosuximide, phensuximide, methsuximide, or a pharmaceutically acceptable salt thereof, for use in the therapeutic treatment of an autistic human's expressive language deficit. In one embodiment, the active pharmaceutical ingredient (ethosuximide, phensuximide, methsuximide, or a pharmaceutically acceptable salt thereof) is administered to an autistic human as described herein: once or twice daily, for at least one month, preferably for at least three months, more preferably for at least six months or longer, to thereby reduce the autistic human's expressive language deficit.

In still another aspect, the invention can be characterized as a medicament having as its active pharmaceutical ingredient one or more of ethosuximide, phensuximide, methsuximide, or a pharmaceutically acceptable salt thereof, for use in the therapeutic treatment of an autistic human's expressive language deficit. Such a medicament can be prepared by compounding the active pharmaceutical ingredient with one or more excipients, nonlimiting examples of which include fillers, carriers, diluents, processing aids, preservatives, coloring agents, and the like.

Other embodiments and modifications within the scope of the invention may be apparent to the skilled person upon reading this disclosure. The invention is limited only by the claims and equivalents thereof.

What is claimed is:

1. A method of treating expressive language deficit in an autistic, nonepileptic human child, comprising:
administering ethosuximide to the autistic, nonepileptic human at a dosage and for a period of time sufficient to reduce the child's expressive language deficit; wherein the dosage is at least 300 mg/day.

2. The method of claim 1, wherein the dosage is 10-60 mg/kg/day (milligrams of ethosuximide per kilogram of body weight per day), provided that the child receives at least 300 mg of ethosuximide per day.

3. The method of claim 1, wherein the period of time is at least six months.

4. The method of claim 2, wherein the dosage is 20-40 mg/kg/day.

5. The method of claim 1, wherein the dosage is 150-1000 mg b.i.d.

6. The method of claim 1, wherein the dosage is 150-500 mg b.i.d.

7. The method of claim 1, wherein the dosage is 500-1000 mg b.i.d.

8. The method of claim 1, wherein the ethosuximide is administered twice per day.

9. The method of claim 1, wherein the ethosuximide is administered orally.

10. The method of claim 1, wherein the dosage and period of time are sufficient to raise the child's expressive language skills by at least 1 point on a 7-point scale, where 0=nonverbal, 1=echolalic, 2=single words, 3=phrases, 4=sentences, 5=spontaneous speech, and 6=mutual speech (true conversation with another person).

11. The method of claim 10, wherein the ethosuximide is administered for a period of time sufficient to raise the child's expressive language skills by at least 1.5 points.

12. The method of claim 10, wherein the ethosuximide is administered for a period of time sufficient to raise the child's expressive language skills by at least 2 points.

13. The method of claim 10, wherein the child has at least normal IQ.

* * * * *